US010695072B2

(12) United States Patent
Rojas et al.

(10) Patent No.: US 10,695,072 B2
(45) Date of Patent: Jun. 30, 2020

(54) KEEL PUNCH SYSTEM

(71) Applicant: b-ONE Ortho, Corp., Cedar Knolls, NJ (US)

(72) Inventors: Joseph Rojas, Midland Park, NJ (US); Juan Martino Fernandez, Miami, FL (US)

(73) Assignee: B-ONE ORTHO, CORP., Cedar Knolls, NJ (US)

( * ) Notice: Subject to any disclaimer, the term of this patent is extended or adjusted under 35 U.S.C. 154(b) by 115 days.

(21) Appl. No.: 16/006,305

(22) Filed: Jun. 12, 2018

(65) Prior Publication Data

US 2019/0374234 A1    Dec. 12, 2019

(51) Int. Cl.
*A61B 17/16* (2006.01)
*A61B 17/00* (2006.01)

(52) U.S. Cl.
CPC ............ *A61B 17/1604* (2013.01); *A61B 2017/00477* (2013.01)

(58) Field of Classification Search
CPC ............ A61B 17/1675; A61B 17/1604; A61B 17/1659; A61B 17/1764; A61F 2/461
See application file for complete search history.

(56) References Cited

U.S. PATENT DOCUMENTS

| 5,356,414 | A * | 10/1994 | Cohen ................ A61B 17/1604 606/86 R |
| 5,690,636 | A | 11/1997 | Wildgoose et al. |
| 8,435,241 | B2 | 5/2013 | Correia et al. |
| 8,852,197 | B2 * | 10/2014 | Waite, II ............ A61B 17/1675 606/84 |
| 8,906,025 | B2 * | 12/2014 | Yoko .................. A61B 17/1764 606/84 |
| 9,345,578 | B2 | 5/2016 | Collazo et al. |
| 2004/0107001 | A1 | 6/2004 | Cheal et al. |
| 2005/0075640 | A1 * | 4/2005 | Collazo .............. A61B 17/1675 606/86 R |
| 2009/0318927 | A1 * | 12/2009 | Martin ............... A61B 17/1764 606/96 |

(Continued)

FOREIGN PATENT DOCUMENTS

EP    1522284    12/2008

OTHER PUBLICATIONS

International Search Report and Written Opinion dated Sep. 11, 2019 for corresponding PCT Application No. PCT/US2019/033730.

*Primary Examiner* — Andrew Yang
(74) *Attorney, Agent, or Firm* — Duane Morris LLP

(57) ABSTRACT

An orthopedic surgical instrument includes a keel punch, an adapter, and a guide tower. The adapter includes an elongate body and a radial locking pin. The guide tower includes a sidewall that defines a passageway configured to receive the keel punch and the adapter. The guide tower also includes one or more L-shaped slots in the sidewall. The adapter and the keel punch lock with each other when the adapter is rotated in a first direction and unlock when the adapter is rotated in a second direction. The locking pin and the L-shaped slot lock with each other when the adapter is rotated in the second direction and unlock when the adapter is rotated in the first direction. Hence, when the adapter is rotated in the second direction for disengaging from the keel punch the locking pin simultaneously engages the L-shaped slot and locks the guide tower to the adapter.

20 Claims, 7 Drawing Sheets

(56) References Cited

U.S. PATENT DOCUMENTS

| | | |
|---|---|---|
| 2010/0076438 A1 | 3/2010 | Correia et al. |
| 2013/0325018 A1 | 12/2013 | Thomas et al. |
| 2014/0094821 A1* | 4/2014 | Wagner ................ A61F 2/461 606/99 |
| 2014/0276858 A1 | 9/2014 | Major et al. |
| 2014/0277546 A1 | 9/2014 | Major et al. |

* cited by examiner

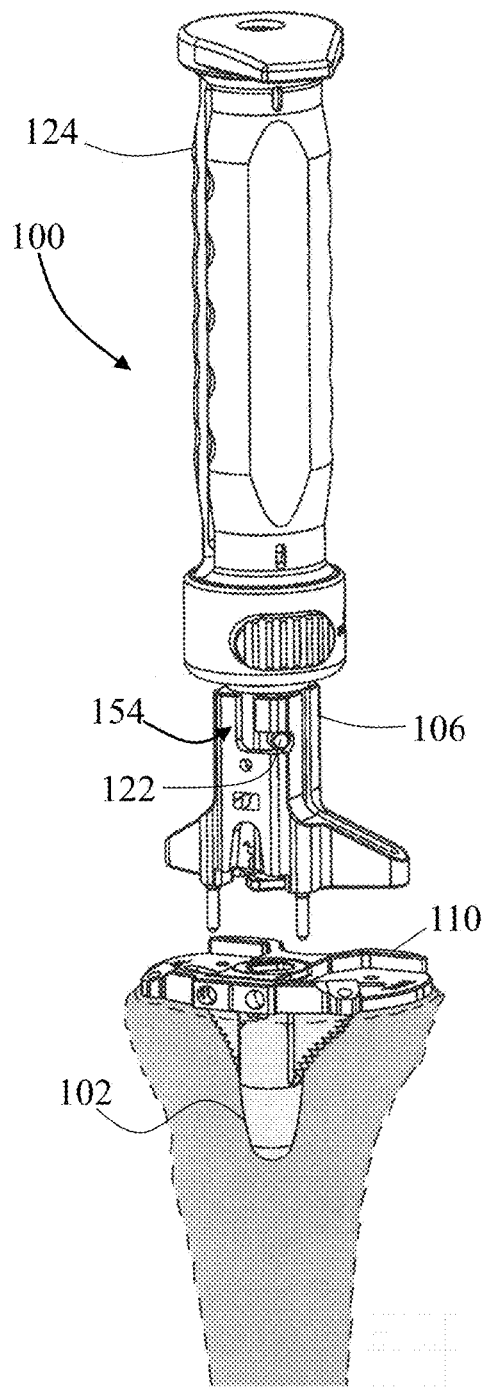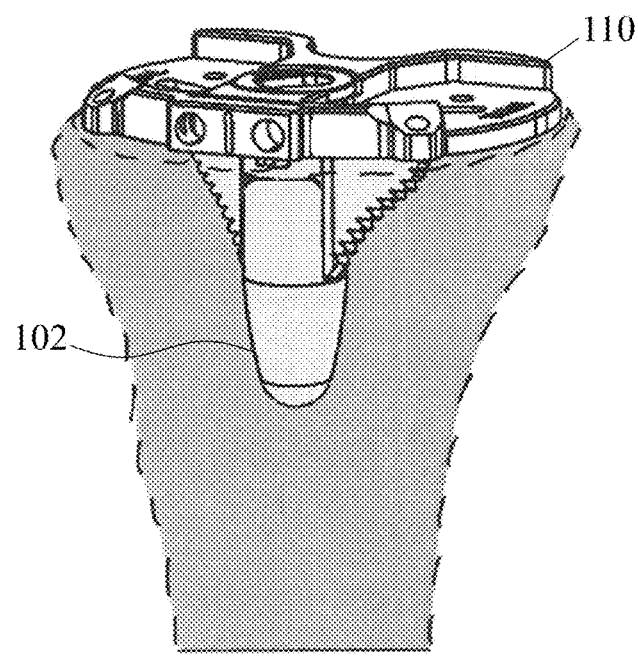
FIG. 3
FIG. 4

KEEL PUNCH SYSTEM

FIELD

The application relates to keel punch systems for use in surgical procedures, specifically for use in forming cavities in a tibial bone.

BACKGROUND

During total knee arthroplasty, portions of the patella, femur and/or tibia are replaced with artificial components. As part of this process, a proximal portion of the tibia and a distal portion of the femur may be resected. The proximal face of the resected tibia must then be prepared for receiving an implant. As part of this preparation, a keel punch can be used to prepare the tibial bone to receive an implant for implantation. The keel punch can be used to create a keeled or finned opening to accept the implant. The corresponding implant can then have a keel or fin shape that prevents rotation of the implant once it has been inserted into the opening.

SUMMARY

In one embodiment, an orthopedic surgical instrument system is disclosed that includes a keel punch, an adapter, and a guide tower. The keel punch has a leading end and a trailing end and is configured to be inserted into a proximal end of a surgically-prepared tibia of a patient. The adapter has a first end and a second end. The second end is configured to removably engage the trailing end of the keel punch. The adapter includes an elongate body between the first end and the second end. A longitudinal axis of the adapter is defined between the first end and the second end. The adapter also includes at least one radial locking pin extending from the elongate body. The trailing end of the keel punch is configured to removably engage the second end of the adapter. The guide tower is configured for guiding the keel punch when the keel punch is being inserted into the proximal end of the surgically-prepared tibia. The guide tower includes a sidewall that defines a passageway that is configured to receive the keel punch and the elongate body of the adapter. One or more L-shaped slots are provided in the sidewall and positioned to engage the at least one radial locking pin. The adapter's second end and the keel punch's trailing end lock with each other when the adapter is axially rotated in a first direction about the longitudinal axis while the second end is engaged with the trailing end of the keel punch and unlock from each other when the adapter is axially rotated in a second direction about the longitudinal axis. The adapter's at least one locking pin and the guide tower's one or more L-shaped slots lock with each other when the adapter is axially rotated in the second direction about the longitudinal axis while the at least one locking pin is engaged in the one or more L-shaped slots and unlock from each other when the adapter is axially rotated in the first direction about the longitudinal axis. Hence, when the adapter is axially rotated in the second direction for disengaging from the keel punch after the keel punch is inserted into the proximal end of the surgically-prepared tibia, the at least one locking pin simultaneously engages the one or more L-shaped slots and locks the guide tower to the adapter.

In another embodiment, an orthopedic surgical instrument system is disclosed that includes a keel punch, an adapter, and a guide tower. The keel punch is configured to be inserted into a proximal end of a surgically-prepared tibia of a patient. The adapter has a first end and a second end, the second end configured to removably engage the keel punch. The adapter includes an elongate body between the first end and the second end and a longitudinal axis of the adapter defined between the first end and the second end. The adapter also includes at least one radial locking pin extending from the elongate body. The adapter also includes a connector extending longitudinally from the second end configured to effectuate the removable engagement of the adapter and the keel punch. The keel punch includes a cavity configured to receive the connector for the removable engagement between the adapter and the keel punch. The guide tower is configured for guiding the keel punch when the keel punch is being inserted into the proximal end of the surgically-prepared tibia. The guide tower includes a sidewall that defines a passageway configured to receive the keel punch and the elongate body of the adapter. The guide tower also includes one or more L-shaped slots provided in the sidewall positioned to engage the at least one locking pin. The adapter's connector and the keel punch's cavity lock with each other when the adapter is axially rotated in a first direction about the longitudinal axis while the adapter's connector is inserted in the keel punch's cavity and unlock from each other when the adapter is axially rotated in a second direction about the longitudinal axis. The adapter's at least one locking pin and the guide tower's one or more L-shaped slots lock with each other when the adapter is axially rotated in the second direction about the longitudinal axis while the at least one locking pin is engaged in the one or more L-shaped slots and unlock from each other when the adapter is axially rotated in the first direction about the longitudinal axis. Hence, when the adapter is axially rotated in the second direction for disengaging from the keel punch after the keel punch is inserted into the proximal end of the surgically-prepared tibia, the at least one locking pin simultaneously engages the one or more L-shaped slots and locks the guide tower to the adapter.

BRIEF DESCRIPTION OF THE DRAWINGS

These and other features and advantages of the screw driver systems described herein will be more fully disclosed in, or rendered obvious by, the following detailed description of the preferred embodiments, which is to be considered together with the accompanying drawings wherein like numbers refer to like parts and further wherein:

FIG. 3 shows a perspective view of the keel punch system of FIG. 1, after disengagement of the adapter from the keel punch and removal of the guide tower from the tibial trial baseplate.

FIG. 4 shows a perspective view of the keel punch system of FIG. 1, after removal of the guide tower.

DETAILED DESCRIPTION

Figure 1:
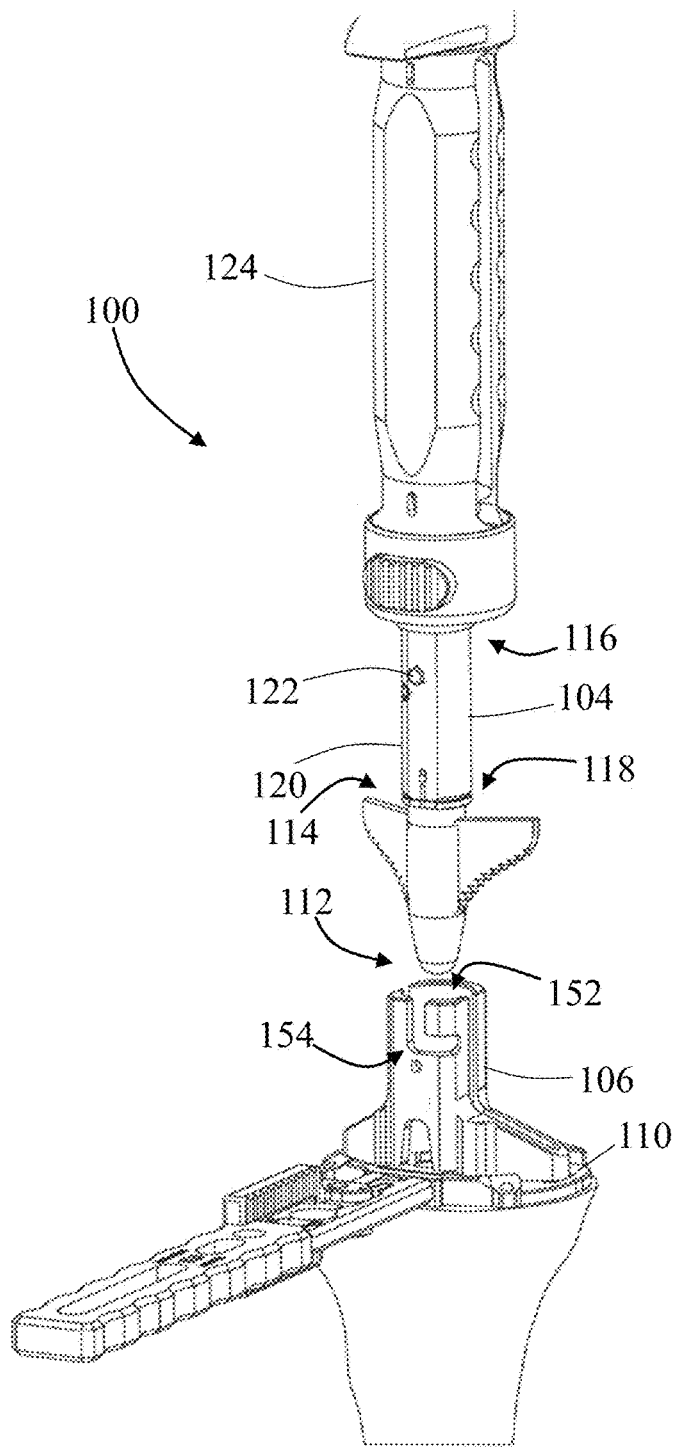
FIG. 1 shows a perspective view of a keel punch system according to one embodiment of the present disclosure, prior to insertion of the keel punch into a tibial bone.

This description of preferred embodiments is intended to be read in connection with the accompanying drawings, which are to be considered part of the entire written description of this invention. The drawing figures are not necessarily to scale and certain features of the invention may be shown exaggerated in scale or in somewhat schematic form in the interest of clarity and conciseness. In the description, relative terms such as "horizontal," "vertical," "up," "down," "top," and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise. The term "operatively or operably connected" is such an attachment, coupling or connection that allows the pertinent structures to operate as intended by virtue of that relationship. In the claims, means-plus-function clauses, if used, are intended to cover the structures described, suggested, or rendered obvious by the written description or drawings for performing the recited function, including not only structural equivalents but also equivalent structures.

The present disclosure describes a keel punch system that can be used by a surgeon or other user to insert a keel punch into a tibia of a patient. The keel punch systems described herein provide a simple method of disengaging the insertion handle from the keel punch after insertion of the keel punch into the tibia. Furthermore, as described herein, the handle can be simultaneously coupled to the guide post of the system to facilitate easy removal of the guide post from the tibia. The systems and methods described herein greater simplify the procedure of inserting the keel punch into the tibia.

As shown in FIG. 1, in one embodiment, an orthopedic surgical instrument system 100 includes a keel punch 102, an adapter 104, and a guide tower 106. The guide tower 106 is configured to engage a tibial trial baseplate 110 to maintain the guide tower 106 in position with respect to the tibia and guide the keel punch 102 when the keel punch 102 is being inserted into the proximal end of a surgically-prepared tibia. A leading end 112 of the keel punch 102 is configured to be inserted into a proximal end of the surgically-prepared tibia of a patient.

Figure 8A:
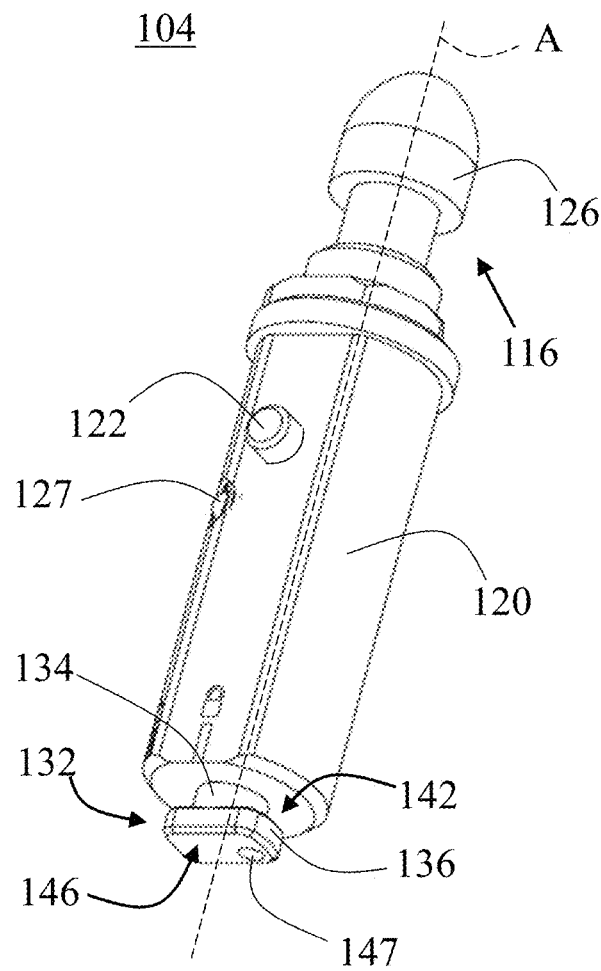
FIG. 8A shows a perspective view of an adapter according to one embodiment of the present disclosure.
Figure 8B:
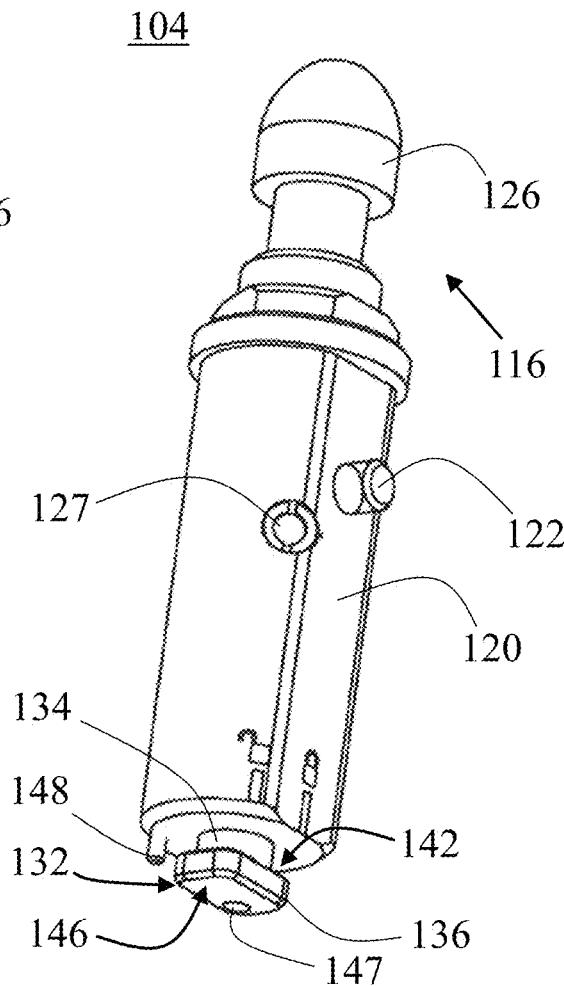
FIG. 8B shows another perspective view of the adapter of FIG. 8A.

As shown in FIGS. 8A and 8B, the adapter 104 has a first end 116 and a second end 118. The second end 118 is configured to removably engage a trailing end 114 of the keel punch 102. The adapter 104 includes an elongate body 120 between the first end 116 and the second end 118. A longitudinal axis A of the adapter 104 is defined between the first end 116 and the second end 118. In addition, at least one radial locking pin 122 extends from the elongate body 120. The radial locking pin 122 can be fixed in position with respect to the elongate body 120 or, alternatively, can be depressible, as will be described further herein. The locking pin 122 can be any appropriate shape. For example, in one embodiment, as shown in FIGS. 8A and 8B, the locking pin 122 is cylindrical.

Figure 2:
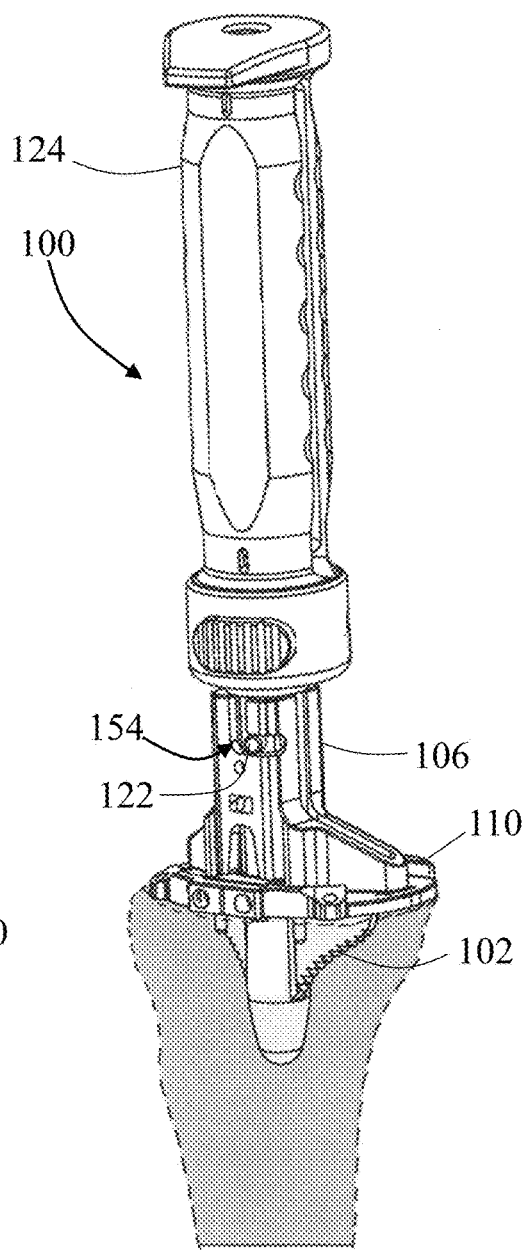
FIG. 2 shows a perspective view of the keel punch system of FIG. 1 after insertion of the keel punch into the tibial bone.

In one embodiment, the keel punch system further includes a handle 124, as shown in FIGS. 1-3. The handle 124 can be configured for ergonomic handling by the user. In one embodiment, the handle 124 can be configured to removably engage with the first end 116 of the adapter 104. Alternatively, in another embodiment, the adapter 104 includes an integrally formed or fixedly coupled handle portion at its first end 116.

Figure 5:
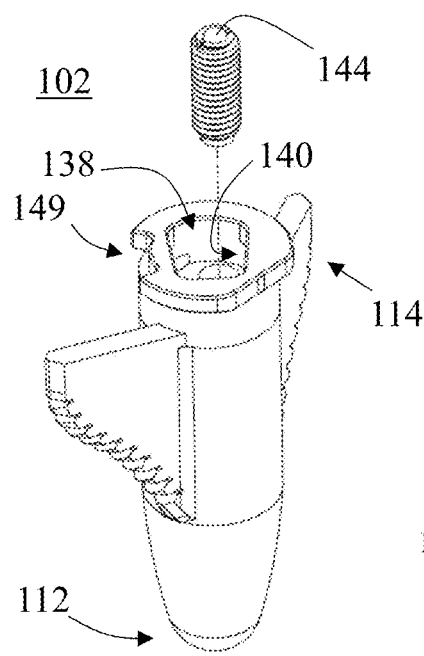
FIG. 5 shows a perspective view of a keel punch according to one embodiment of the present disclosure.
Figure 6:
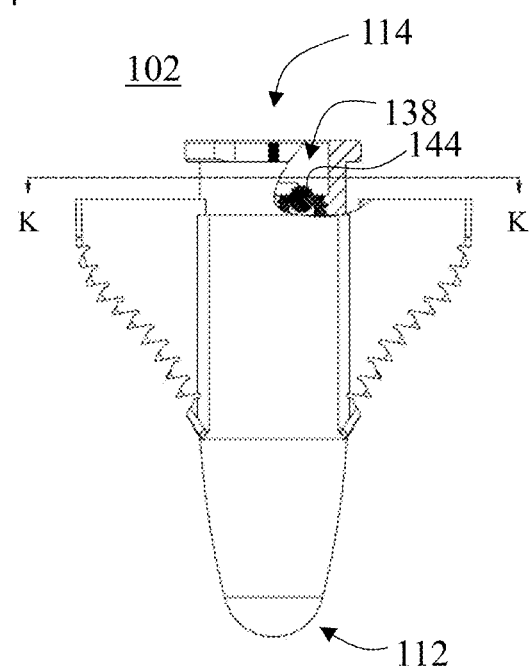
FIG. 6 shows a front view of the keel punch of FIG. 5.
Figure 7:
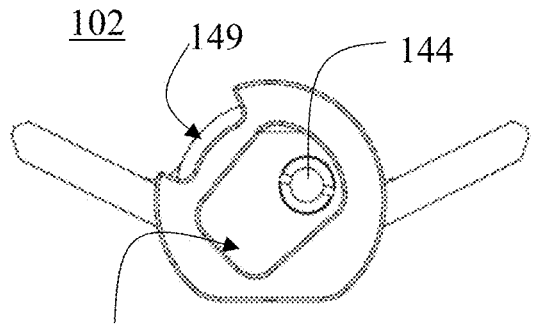
FIG. 7 shows a top view of the keel punch of FIG. 5.

In one embodiment, to effectuate the locking, the second end 118 of the adapter 104 is provided with a connector 132, as shown in FIGS. 8A and 8B. The connector 132 includes a post 134 extending from the elongate body 120 and a flattened key 136 engaged with the post 134 at an end of the post 134 opposite the elongate body 120. As shown in FIGS. 5-7, the trailing end 114 of the keel punch 102 is provided with a cavity 138 to receive the connector 132 such that the adapter 104 and the keel punch 102 can be removably engaged. In one embodiment, the cavity 138 includes a shoulder 140 configured such that when the adapter 104 is locked with the keel punch 102, the shoulder 140 is in contact with a proximal face 142 of the flattened key 136. Further, the keel punch 102 can include a biased member 144 disposed at least partially within the cavity 138. With the adapter 104 and the keel punch 102 removably engaged, the biased member 144 contacts a distal face 146 of the flattened key 136 to maintain contact of the proximal face 142 with the shoulder 140. In one embodiment, the distal face 146 of the adapter 104 includes an indentation 147 to receive or engage a portion of the biased member 144. The engagement of the biased member 144 of the keel punch 102 with the indentation 147 can resist rotation of the adapter 104 with respect to the keel punch 102. This prevents any unintended or arbitrary rotation of the adapter 104 with respect to the keel punch 102. In addition, when the spring member 144 engages the indentation 147, it can produce tactile or audible feedback that indicates to the operator that the adapter 104 is locked with the keel punch 102.

The biased member 144 can be any appropriate feature or component for imparting a force on the flattened key 136 to maintain contact of the proximal face 142 with the shoulder 140. In one embodiment, as shown in FIGS. 5-7, the biased member is a spring plunger with a ball or rod biased toward an extended position by a spring. In such embodiments, the ball or rod can engage the indentation 147 on the distal face 146 of the flattened key 136. In other embodiments, the biased member 144 is a spring, such as a helical compression spring, a conical spring, or a Belleville washer. In another embodiment, the biased member 144 is an elastomeric member.

As shown in FIG. 8B, in one embodiment, the adapter 104 includes an orientation key 148 protruding from the second end 118 of the elongate body 120. Additionally, as shown in FIG. 5, the keel punch 102 includes a corresponding recess 149 configured to receive the orientation key 148 and allow the adapter 104 and the keel punch 102 to engage each other only in a predetermined angular relationship about the longitudinal axis A.

Returning to FIGS. 8A and 8B, in one embodiment, the adapter 104 includes an extension 126 provided at the first end 116 that extends from the elongate body 120 for removably engaging with a universal handle such as the handle 124 shown in FIGS. 1 and 2. The handle 124 can be configured to engage the extension 126 so that the handle can be used to turn the adapter 104. For example, although not shown here, the handle 124 can be provided with a recess for receiving the extension 126. In at least one embodiment, the rotational orientation of the adapter 104 is fixed with respect to the handle 124 when the adapter 104 is engaged with the handle. In some embodiments, the handle 124 and the adapter 104 are integrally formed as a one-piece unit.

Referring to FIGS. 1-3, 5, and 8, the trailing end 114 of the keel punch 102 is configured to removably engage the second end 118 of the adapter 104. The second end 118 of the adapter 104 and the trailing end 114 of the keel punch 102 lock with each other when the adapter 104 is axially rotated in a first direction about the longitudinal axis A while the second end 118 is engaged with the trailing end 114 of the keel punch 102. Conversely, the second end 118 of the adapter 104 and the trailing end 114 of the keel punch 102 unlock from each other when the adapter 104 is axially rotated in an opposite second direction about the longitudinal axis A. For example, in one embodiment, a clockwise rotation of the adapter 104 with respect to the keel punch 102 after engaging the second end 118 of the adapter 104 with the trailing end of the keel punch 102 locks the adapter 104 and the keel punch 102. A counter-clockwise rotation of the adapter 104 unlocks the adapter 104 and the keel punch 102.

Figure 9:
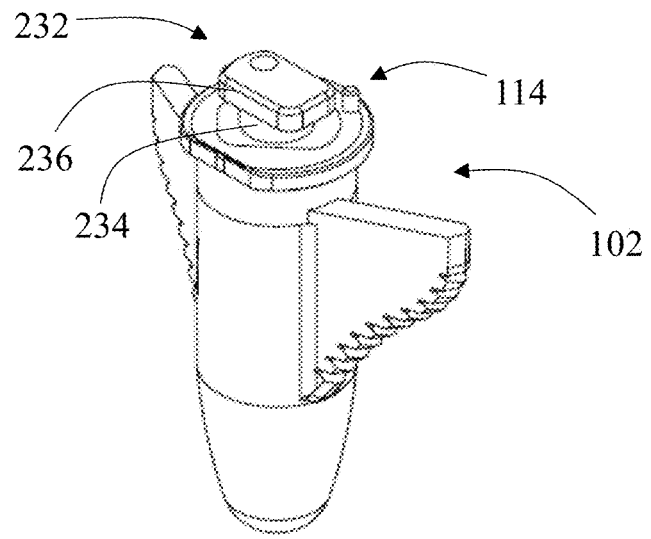
FIG. 9 shows a perspective view of a keel punch according to another embodiment of the present disclosure.
Figure 10:
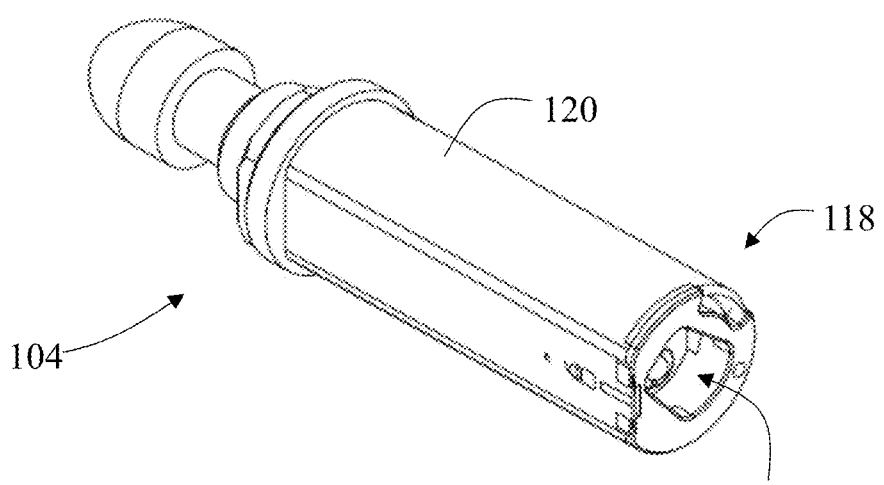
FIG. 10 shows a perspective view of an adapter according to another embodiment of the present disclosure.

In another embodiment, as shown in FIGS. 9 and 10, the connecting structures on the adapter 104 and the keel punch 102 are swapped from the embodiment shown in FIGS. 5 and 8. In this embodiment, the trailing end 114 of the keel punch 102 is provided with a male connector structure 232 configuration similar to the male connector structure 132 on the second end 118 of the adapter 104 shown in FIG. 9. In turn, as shown in FIG. 10, the second end 118 of the adapter 104 is provided with a cavity 238 configuration for receiving the male connector structure 232 similar to the cavity 138 configuration on the trailing end 114 of the keel punch 102 shown in FIG. 5. The connector structure 232 includes a flattened key 236 connected to the trailing end 114 of the keel punch 102 by a post 234. In such an embodiment, the locking and unlocking of the adapter 104 and the keel punch 102 operates substantially similar to the adapter and keel punch embodiment illustrated in FIGS. 5-8.

Figure 11:
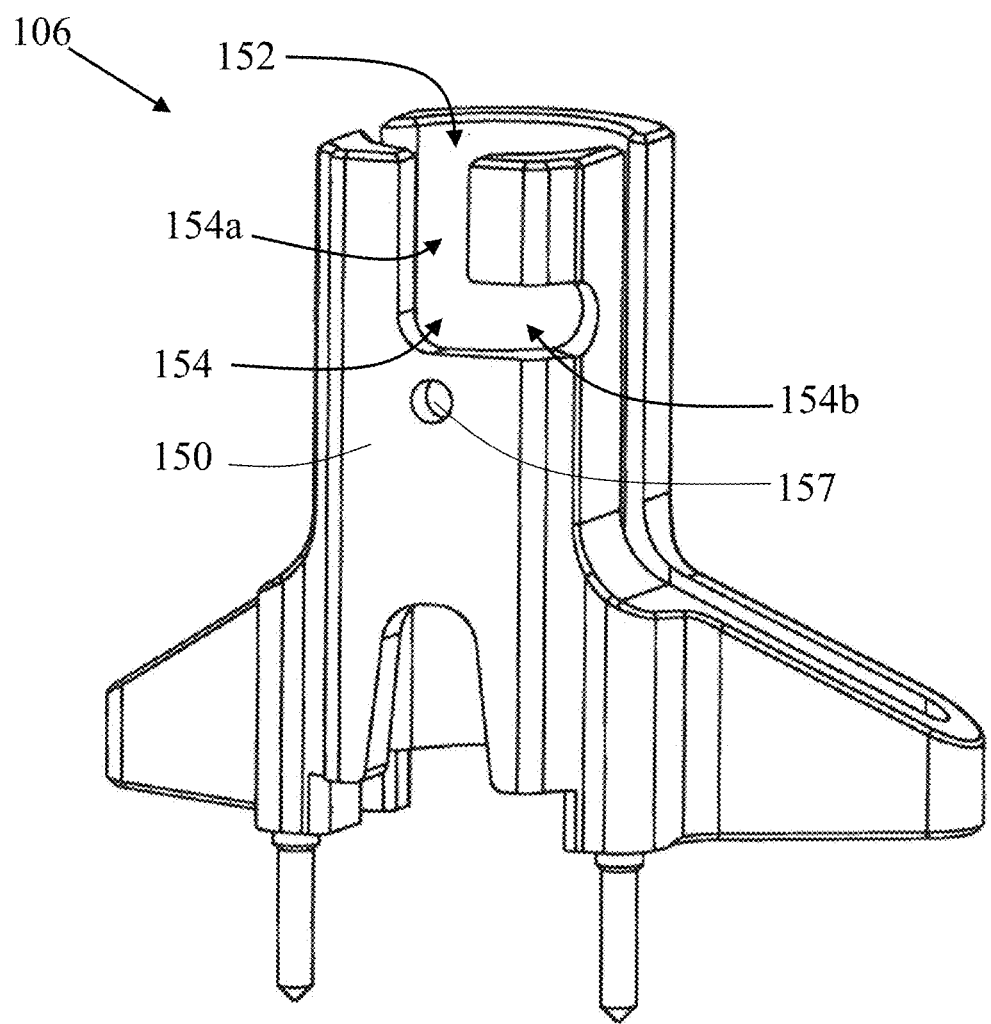
FIG. 11 shows a perspective view of a guide tower according to one embodiment of the present disclosure.

As shown in FIG. 11, the guide tower 106 includes a sidewall 150 that defines a passageway 152 that is configured to receive the keel punch 102 and the elongate body 120 of the adapter 104. The guide tower also includes one or more L-shaped slots 154 provided in the sidewall 150. The one or more L-shaped slots 154 are positioned to engage the at least one radial locking pin 122. The L-shaped slots 154 include a first leg 154a and a second leg 154b. In one embodiment, the first leg 154a and the second leg 154b are substantially perpendicular. In other embodiments, the first leg 154a and the second leg 154b are at an angle other than perpendicular. For example, in one embodiment, the second leg 154b defines an acute angle with respect to the first leg 154a such that the second leg 154b is turned upward.

The locking pin 122 of the adapter 104 and the L-shaped slot 154 of the guide tower 106 lock with each other when the adapter 104 is axially rotated in the second direction about the longitudinal axis A while the locking pin 122 is engaged in the L-shaped slot 154. Conversely, the locking pin 122 disengages from the L-shaped slot 154 when the adapter 104 is axially rotated in the first direction about the longitudinal axis A. Specifically, the locking pin 122 is inserted into the first leg 154a until it is aligned with the second leg 154b. The adapter 104 is then rotated in the second direction to cause the locking pin to travel into the second leg 154b. The adapter 104 and the guide tower 106 are thereby locked together in a sense that the adapter 104 cannot travel in the axial direction within the guide tower 106.

The structural features of the keel punch 102, the adapter 104 and the guide tower 106 described above enables the keel punch 102 with the adapter 104 attached to it to be punched into a desired position in the tibia guided by the guide tower 106, as shown in FIG. 2, then with a single motion, simultaneously disengage the adapter 104 from the keel punch 102 and engage the adapter 104 and the guide tower 106 together. Then, the guide tower 106 can be removed from its position on the tibia while leaving behind the keel punch 102. When the adapter 104 is axially rotated in the second direction for disengaging from the keel punch 102 after the keel punch 102 is inserted into the proximal end of the tibia, the locking pin 122 on the adapter 104 simultaneously engages the L-shaped slot 154 and locks the adapter 104 to the guide tower 106. Hence, the single motion of rotating the adapter 104 disengages the keel punch 102 from the adapter 104 and engages the adapter 104 to the guide tower 106 simultaneously. After the locking pin 122 engages with the L-shaped slot 154, the guide tower 106 can be removed in the axial direction from the tibial trial baseplate 110 using the adapter 104 while leaving behind the keel punch 102.

Figure 12:
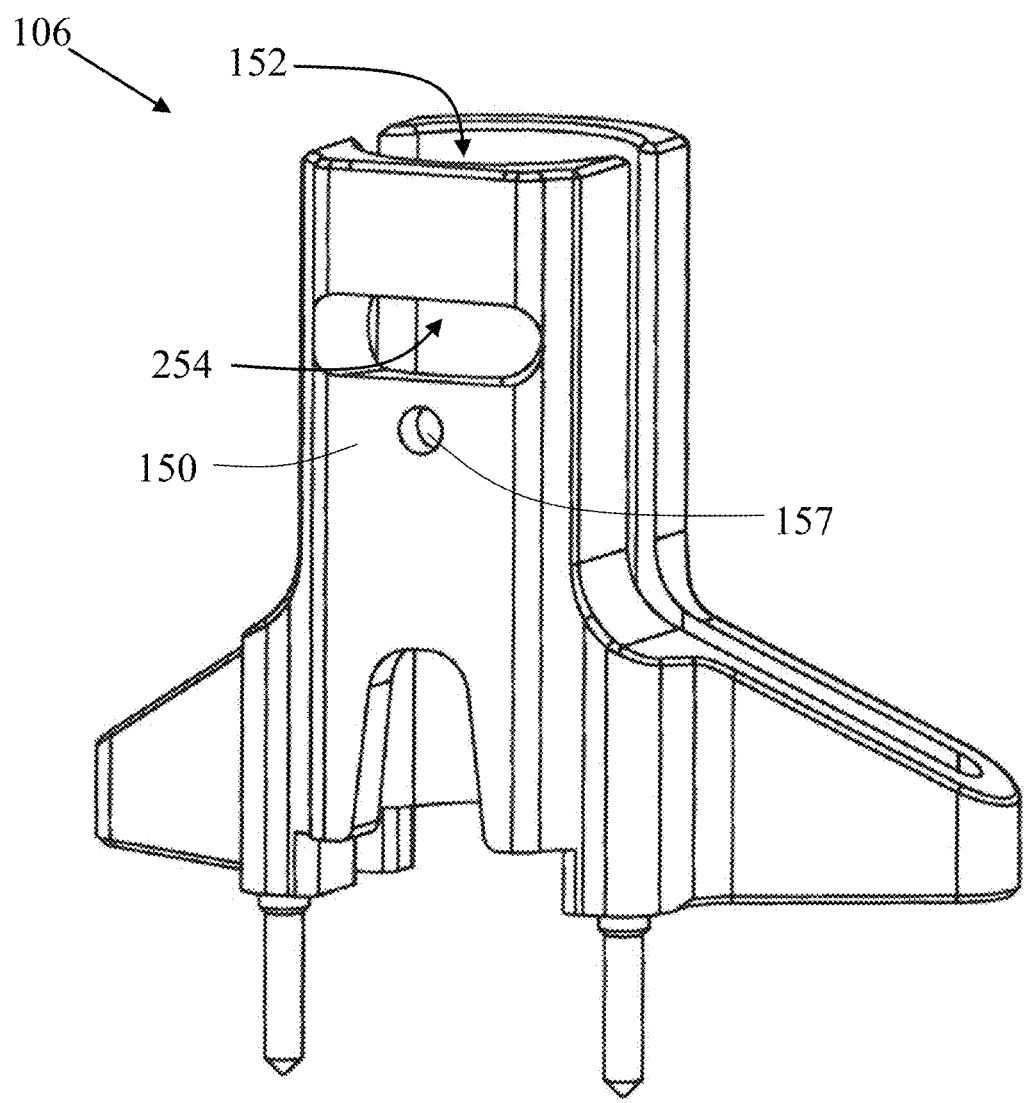
FIG. 12 shows a perspective view of a guide tower according to another embodiment of the present disclosure.

As shown in FIG. 12, in an alternative embodiment of the guide tower 106A, the locking pin 122 on the adapter 104 is a depressible button and the guide tower 106A is provided with a single slot 254 oriented similarly to the second leg 154b of the guide tower 106A described above. In such an embodiment, the locking pin 122 is compressed into the adapter 104 body as the adapter/keel punch assembly is inserted into the guide tower 106A and as the depressible locking pin 122 contacts the top edge of the sidewall 150 of the guide tower 106A the locking pin 122 is forced into a depressed position. The inner surface of the top edge of the guide tower 106A can optionally include a ramped or a chamfered surface to better facilitate depression of the locking pin 122. When the adapter/keel punch assembly is fully inserted into the guide tower 106A, the locking pin 122 is aligned with the slot 254. Once aligned, the depressible locking pin 122 will pop out of its compressed state to its fully extended position and extend into the slot 254, thus engaging the adapter 104 and the guide tower 106A together. Because the slot 254 is elongated in the same manner as the second leg 154b of the embodiment shown in FIG. 11, the slot 254 accommodates the locking pin 122 to travel within the slot 254 and allows the adapter 104 to be rotated for unlocking the adapter 104 from the keel punch 102. the locking pin 122. As described above, once the adapter 104 is unlocked from the keel punch 102, the guide tower 106A can be removed from the tibial trial baseplate 110 using the adapter 104 which is now attached to the guide tower 106A by the locking pin 122 being trapped in the slot 154.

In some embodiments, the adapter 104 is provided with a second biased member 127 on the exterior of the elongate body 120 and the guide towers 106 and 106A are provided with corresponding receiving structure 157 for receiving the second biased member 127. The second biased member 127 is shown in FIGS. 8A and 8B. The corresponding structure 157 on the guide tower 106, 106A is shown in FIGS. 11 and 12. The second biased member 127 is structured similar to the first biased member 144 discussed above. The receiving structure 157 on the guide tower 106, 106A can be a hole as shown in the illustrated embodiments or it can be an indentation or a relief provided on the interior surface of the sidewall 150. The location of the second biased member 127 on the adapter 104 with respect to the locking pin 122 and, in turn, the location of the receiving structure 157 on the guide tower 106, 106A with respect to the slots 154, 254 are arranged so that the second biased member 127 and the receiving structure 157 engage each other when the adapter 104 is rotated into the locked position within the slots 154, 254. This resists the adapter 104 from unintendedly rotating back in reverse direction into an unlocked position.

A method of operating the surgical instrument system 100 is also provided. The steps of inserting the keel punch 102 and removing the guide tower 106 are shown in detail in FIGS. 1-4. First, as shown in FIGS. 1 and 2, the keel punch 102 and adapter 104 are inserted through the passageway 152 of the guide tower 106 and the keel punch 102 is inserted into the tibia. As shown in FIG. 2, the adapter 104 is then rotated in the second direction (counter-clockwise in the embodiment illustrated) to disengage the adapter 104 from the keel punch 102 and engage the locking pin 122 with the L-shaped slot 154. As shown in FIG. 3, the guide tower 106 can then be removed from the tibial trial baseplate 110 using the adapter 104. After removal of the guide tower 106, the keel punch 102 and tibial trial baseplate 110 remain in place, as shown in FIG. 4.

While the foregoing description and drawings represent preferred or exemplary embodiments of the present invention, it will be understood that various additions, modifications and substitutions may be made therein without departing from the spirit and scope and range of equivalents of the accompanying claims. In particular, it will be clear to those skilled in the art that the present invention may be embodied in other forms, structures, arrangements, proportions, sizes, and with other elements, materials, and components, without departing from the spirit or essential characteristics thereof. In addition, numerous variations in the methods/processes described herein may be made without departing from the spirit of the invention. One skilled in the art will further appreciate that the invention may be used with many modifications of structure, arrangement, proportions, sizes, materials, and components and otherwise, used in the practice of the invention, that are particularly adapted to specific environments and operative requirements without departing from the principles of the present invention. The presently disclosed embodiments are therefore to be considered in all respects as illustrative and not restrictive, the scope of the invention being defined by the appended claims and equivalents thereof, and not limited to the foregoing description or embodiments. Rather, the appended claims should be construed broadly, to include other variants and embodiments of the invention, that may be made by those skilled in the art without departing from the scope and range of equivalents of the invention. All patents and published patent applications identified herein are incorporated herein by reference in their entireties.

We claim:

1. An orthopedic surgical instrument system comprising:
a keel punch having a leading end and a trailing end, and configured to be inserted into a proximal end of a surgically-prepared tibia of a patient;
an adapter having a first end and a second end, the second end configured to removably engage the trailing end of the keel punch, wherein the adapter comprises:
an elongate body between the first end and the second end;
a longitudinal axis of the adapter defined between the first end and the second end; and
at least one radial locking pin extending from the elongate body;
wherein the trailing end of the keel punch is configured to removably engage the second end of the adapter; and
a guide tower for guiding the keel punch when the keel punch is being inserted into the proximal end of the surgically-prepared tibia, the guide tower comprising:
a sidewall that defines a passageway configured to receive the keel punch and the elongate body of the adapter; and
one or more L-shaped slots provided in the sidewall positioned to engage the at least one radial locking pin;
wherein the adapter's second end and the keel punch's trailing end lock with each other when the adapter is axially rotated in a first direction about the longitudinal axis while the second end is engaged with the trailing end of the keel punch and unlock from each other when the adapter is axially rotated in a second direction about the longitudinal axis;
wherein the adapter's at least one locking pin and the guide tower's one or more L-shaped slots lock with each other when the adapter is axially rotated in the second direction about the longitudinal axis while the at least one locking pin is engaged in the one or more L-shaped slots and unlock from each other when the adapter is axially rotated in the first direction about the longitudinal axis; and
whereby when the adapter is axially rotated in the second direction for disengaging from the keel punch after the keel punch is inserted into the proximal end of the surgically-prepared tibia, the at least one locking pin simultaneously engages the one or more L-shaped slots and locks the guide tower to the adapter.

2. The orthopedic surgical instrument system of claim 1, wherein the first direction and the second direction are in opposite directions.

3. The orthopedic surgical instrument system of claim 1, wherein the first end of the adapter is an integrally formed handle portion.

4. The orthopedic surgical instrument system of claim 1, further comprising a handle, wherein the handle and the first end of the adapter are configured to removably engage each other.

5. The orthopedic surgical instrument system of claim 4, wherein the adapter further comprises an extension extending from the elongate body and the handle comprises a recess and an engagement member, the recess sized to receive the extension and the engagement member configured to engage the extension to retain the extension within the recess, and wherein the rotational orientation of the adapter is fixed with respect to the handle when the extension is retained within the recess.

6. The orthopedic surgical instrument system of claim 1, wherein the second end of the adapter is provided with a connector comprising a post extending from the elongate body and a flattened key engaged with the post at an end opposite the elongate body, and the trailing end of the keel punch is provided with a cavity to receive the connector for the removable engagement between the adapter and the keel punch.

7. The orthopedic surgical instrument system of claim 1, wherein the trailing end of the keel punch is provided with a connector comprising a post extending from the trailing end of the keel punch and a flattened key engaged with the post at an end opposite the trailing end, and the second end of the adapter is provided with a cavity to receive the connector for the removable engagement between the adapter and the keel punch.

8. The orthopedic surgical instrument system of claim 1, further comprising a tibial trial baseplate, wherein the trial baseplate is configured to removably engage the guide tower.

9. The orthopedic surgical instrument system of claim 1, wherein the at least one locking pin is a cylindrical pin.

10. The orthopedic surgical instrument system of claim 1, wherein the adapter further comprises an orientation key protruding from the second end of the elongate body, and further wherein the trailing end of the keel punch comprises a corresponding recess configured to receive the orientation key and allowing the adapter and the keel punch to engage each other only in predetermined angular relationship about the longitudinal axis.

11. An orthopedic surgical instrument system comprising:
a keel punch configured to be inserted into a proximal end of a surgically-prepared tibia of a patient;
an adapter having a first end and a second end, the second end configured to removably engage the keel punch, wherein the adapter comprises:
an elongate body between the first end and the second end;
a longitudinal axis of the adapter defined between the first end and the second end;
at least one radial locking pin extending from the elongate body; and
a connector extending longitudinally from the second end configured to effectuate the removable engagement of the adapter and the keel punch;
wherein the keel punch includes a cavity configured to receive the connector for the removable engagement between the adapter and the keel punch; and
a guide tower for guiding the keel punch when the keel punch is being inserted into the proximal end of the surgically-prepared tibia, the guide tower comprising:
a sidewall that defines a passageway configured to receive the keel punch and the elongate body of the adapter; and
one or more L-shaped slots provided in the sidewall positioned to engage the at least one locking pin;
wherein the adapter's connector and the keel punch's cavity lock with each other when the adapter is axially rotated in a first direction about the longitudinal axis while the adapter's connector is inserted in the keel punch's cavity and unlock from each other when the adapter is axially rotated in a second direction about the longitudinal axis;
wherein the adapter's at least one locking pin and the guide tower's one or more L-shaped slots lock with each other when the adapter is axially rotated in the second direction about the longitudinal axis while the at least one locking pin is engaged in the one or more L-shaped slots and unlock from each other when the adapter is axially rotated in the first direction about the longitudinal axis; and
whereby when the adapter is axially rotated in the second direction for disengaging from the keel punch after the keel punch is inserted into the proximal end of the surgically-prepared tibia, the at least one locking pin simultaneously engages the one or more L-shaped slots and locks the guide tower to the adapter.

12. The orthopedic surgical instrument system of claim 11, wherein the first direction and the second direction are in opposite directions.

13. The orthopedic surgical instrument system of claim 11, wherein the first end of the adapter is an integrally formed handle portion.

14. The orthopedic surgical instrument system of claim 11, further comprising a handle, wherein the handle and the first end of the adapter are configured to removably engage each other.

15. The orthopedic surgical instrument system of claim 14, wherein the adapter further comprises an extension extending from the elongate body and the handle comprises a recess and an engagement member, the recess sized to receive the extension and the engagement member configured to engage the extension to retain the extension within the recess, wherein the rotational orientation of the adapter is fixed with respect to the handle when the extension is retained within the recess.

16. The orthopedic surgical instrument system of claim 11, further comprising a tibial trial baseplate, wherein the trial baseplate is configured to removably engage the guide tower.

17. The orthopedic surgical instrument system of claim 11, wherein the connector comprises:
a post extending from the elongate body and
a flattened key engaged with the post at an end opposite the elongate body.

18. The orthopedic surgical instrument system of claim 17, wherein the cavity of the keel punch includes a shoulder configured such that when the adapter is removably engaged with the keel punch, the shoulder is in contact with a proximal face of the flattened key.

19. The orthopedic surgical instrument system of claim 18, wherein the keel punch includes a biased member disposed at least partially within the cavity, and wherein the biased member contacts a distal face of the flattened key when the adapter is removably engaged with the keel punch and applies a force on the flattened key to maintain contact of the proximal face with the shoulder.

20. The orthopedic surgical instrument system of claim 11, wherein the adapter further comprises an orientation key protruding from the second end of the elongate body, and further wherein the keel punch comprises a corresponding recess configured to receive the orientation key and allowing the adapter and the keel punch to engage each other only in predetermined angular relationship about the longitudinal axis.

* * * * *